United States Patent [19]

Kradolfer et al.

[11] 4,263,280

[45] Apr. 21, 1981

[54] SYNERGISTIC MIXTURES

[75] Inventors: Friedrich Kradolfer, Basel; Otokar Zak, Birsfelden, both of Switzerland

[73] Assignee: Ciba-Geigy Corporation, Ardsley, N.Y.

[21] Appl. No.: 28,032

[22] Filed: Apr. 9, 1979

[30] Foreign Application Priority Data

Apr. 19, 1978 [CH] Switzerland ...................... 4194/78

[51] Int. Cl.³ .............................................. A61K 35/00
[52] U.S. Cl. .................................................... 424/114
[58] Field of Search ........................................ 424/114

[56] References Cited

FOREIGN PATENT DOCUMENTS 2234280 2/1973 Fed. Rep. of Germany ........... 424/246

OTHER PUBLICATIONS

Nomura et al., J. of Antibiotics, vol. XXIX, No. 9, Sep. 1976, pp. 928–936.
PDR, 27 ed., 1973, pp. 1258–1259.

Primary Examiner—Jerome D. Goldberg
Attorney, Agent, or Firm—Prabodh I. Almaula

[57] ABSTRACT

The invention relates to new synergistic mixtures which contain, as active components, the antibiotic cefsulodin sodium and a second known antibiotic selected from the group comprising the β-lactamase inhibitors, penicillins, cephalosporins or aminoglycosides, pharmaceutical preparations containing said mixtures and a process for their manufacture, and to the use of these preparations for combating infections.

3 Claims, No Drawings

SYNERGISTIC MIXTURES

The present invention relates to new synergistic mixtures of antibiotic compounds having properties superior to those of the individual components, pharmaceutical preparations containing said mixtures and processes for their manufacture, and the use of said preparations for combating infections.

The synergistic mixtures of the invention contain, as active components, the antibiotic cefsulodin sodium and a second known antibiotic selected from the groups comprising the β-lactamase inhibitors, penicillins, cephalosporins or aminoglycosides.

Cefsulodin sodium is the international non-proprietory name for the sodium salt of N-[7β-(α-sulfophenylacetamido)ceph-3-em-3-yl-methyl]-4′-carbamoylpyridinium-4-carboxylate. The compound is known from German Offenlegungsschrift No. 2,234,280. Its antibiotic action is directed against Gram-negative cocci, Gram-positive cocci and bacteria, and especially against Pseudomonas strains, both carbenicillin-sensitive and carbenicillin-resistant. Cefsulodin sodium has a relatively insignificant action against enterobacteria, such as *Escherichia coli* and *Klebsiella pneumoniae*, and *anaerobei*, for example Bacteroides.

The present invention is based on the surprising observation that the antibiotic action of antibiotics selected from the groups comprising the β-lactamase inhibitors, penicillins, cephalosporins and aminoglycosides, and that of cefsulodin sodium, intensify in synergistic manner in the mixtures of the invention, and that in some cases there is even an increase in the tolerance to the individual components. This synergism has also surprisingly been observed in the case of enterobacteria, anaerobei and polyinfections.

The advantages of synergistic mixtures over the individual components of which they consist are well known and can be utilised in various ways. The advantages of the antibiotic mixtures of this invention reside both in a reduction of the dose while achieving the same effect (which means imposing less of a strain on the organism with foreign substances and consequently diminishing the side-effects) and in a broadening of the activity spectrum (which is of importance in the treatment of polyinfections, especially of secondary infections in Pseudomonas infections). Furthermore, a reduced tendency to develop resistant strains is to be expected. By means of a suitable combination it is also possible to combat strains which are not inhibited by the individual components.

Examples of suitable β-lactamase inhibitors for the synergistic mixtures of the present invention which are themselves known to have insignificant antibiotic action, are clavulanic acid (U.S. Pat. No. 4,087,067) and penicillanic acid 4,4-dioxide (CP-45.899, The Journal of Antibiotics, Vol. XXXI, No. 12, 1978, 1238).

Suitable penicillins and cephalosporins are to be found in the comprehensive publications of E. H. Flynn, Cephalosporins and Penicillins, Academic Press, New York and London, 1972, P. G. Sammes, Chem. Rev., 1976, Vol. 76, No. 1, pages 113–155, J. Cs. Jászberényi and T. E. Gunda, Progr. Med. Chem., Vol. 12, 1975, pages 395–477, J. Elks, Recent Advances in the Chemistry of β-Lactam Antibiotics, The Chemical Society, Burlington House, London WIV OBN, 1977, the patent specifications cited hereinafter, or in the Merck Index, 9th Edition, Merck+Co. Inc., Rahway, N.J., U.S.A., 1976.

Suitable penicillins are, for example, those selected from the groups comprising the carboxypenicillins, sulfopenicillins, ureidopenicillins and methyleneaminopenicillins.

The groups of the carboxy- and sulfopenicillins comprise, for example, 6β-(2-$R_1$-2-$R_2$-acetylamino)penicillanic acids, wherein $R_1$ represents phenyl, thienyl, such as 2- or 3-thienyl, or furyl, such as 2- or 3-furyl, and $R_2$ represents carboxy which is free or esterified e.g. by phenyl or indanyl, or sulfo, and the salts thereof, for example the sodium salts. Examples of such penicillins to be singled out for special mention are carbenicillin ($R_1$=phenyl, $R_2$=carboxyl, sodium salt), carfecillin ($R_1$=phenyl, $R_2$=phenoxycarbonyl), indanylcarbenicillin ($R_1$=phenyl, $R_2$=indanyloxycarbonyl), ticarcillin ($R_1$=3-thienyl, $R_2$=carboxyl, disodium salt), and sulfocillin (sulbenicillin) ($R_1$=phenyl, $R_2$=sulfo).

Examples of suitable ureidopenicillins for the synergistic mixtures of the invention are known from German Offenlegungsschrift Nos. 2,152,967 and 2,152,968 and from Belgian Pat. Nos. 843,342 and 862,273. Representatives falling under this group to be singled out for special mention are the 6β-[D-2-(2-oxo-3-X-imidazol-1-yl-carbonylamino)phenylacetylamino]penicillanic acids, wherein X is hydrogen or a substituent, for example an acyl group, such as lower alkanoyl, for example formyl or acetyl, arylcarbonyl, for example benzoyl or furoyl, lower alkoxycarbonyl, for example methoxy- or isopropoxycarbonyl, aryloxycarbonyl, for example phenyloxycarbonyl, unsubstituted or N-substituted carbamoyl, for example carbamoyl, N-methylcarbamoyl or 1-pyrrolidylcarbonyl, or, in particular, lower alkylsulfonyl, for example methyl- or ethylsulfonyl, or wherein X is a substituted or unsubstituted methylideneimino group, in which the methylidene moiety is substituted for example by cycloalkyl, for example cyclopropyl, by 5- or 6-membered aromatic heterocyclyl, for example furyl or pyridyl, and wherein the phenyl moiety is unsubstituted or substituted, preferably in the para-position, by nitro, lower alkyl, such as methyl, halogen, such as chlorine, unsubstituted or substituted amino, such as acetylamino, hydroxyl, lower alkoxy, such as methoxy, or lower alkylsulfonyl, especially methylsulfonyl. Such ureidopenicillins are in particular azlocillin (X=hydrogen), mezlocillin (X=methylsulfonyl); and Bay k4999 (X=3-furyl-methylideneimino, phenyl substituted in the 4-position by hydroxyl). Further ureidopenicillins are known from Netherlands published patent application No. 7,609,539. Attention is drawn in particular to the 6β-[D-2-(4-A-2,3-dioxo-1-piperazinocarboxamido)phenylacetamido]penicillanic acids, wherein A is hydrogen or a substituent, for example one of those referred to in the definition of X above, or, in particular, lower alkyl, such as methyl or ethyl. Piperacillin (A=ethyl) is of particular interest. The ureidopenicillins are preferably used as salts, especially as sodium salts.

Suitable methyleneaminopenicillins are, for example, those known from German Offenlegungsschrift Nos. 2,055,531 and 2,123,111, in particular the 6β-(1-azacyclylmethyleneamino)-penicillanic acids, especially mecillinam (1-azacyclyl=hexahydro-1H-azepin-1-yl) and the salts thereof, such as the sodium salts.

Suitable cephalosporins are those which are active when applied parenterally. Cephalosporins to be singled out for special mention are: 7β-(2-$R_1$-2-$R_2$- acetamido)-7α-$R_3$-3-$R_4$-3-cephem-4-carboxylic acids, wherein $R_1$ is hydrogen or a mono- or divalent substituent, for example hydroxyl, unsubstituted or acylated amino, hydroximino or lower alkoximino, such as cis-methoximino, $R_2$ is cyano, phenyl, thienyl, furyl, tetrazolyl or thiazolyl which rings are unsubstituted or substituted by hydroxyl, unsubstituted or substituted amino, such as lower alkylsulfonylamino, for example methylsulfonylamino, or by aminomethyl, such as phenyl, p-hydroxyphenyl, m-methylsulfonylaminophenyl, 2-thienyl, 5-aminomethyl-2-thienyl, 2-furyl, 1-tetrazolyl, and, in particular, 2-aminothiazol-4-yl (isomer with 2-imino-4-thiazolin-4-yl), $R_3$ is hydrogen or lower alkoxy, such as methoxy, and $R_4$ is lower alkoxy, such as methoxy, lower alkanoyloxymethyl, such as acetoxymethyl, carbamoyloxymethyl, or heterocyclylthiomethyl, wherein heterocyclyl is pyridyl, N-oxopyridyl, pyrimidyl, pyridazinyl, N-oxopyridazinyl, pyrazolyl, imidazolyl, thiazolyl, 1,2,3-thiadiazolyl, 1,2,4-thiadiazolyl, 1,3,4-thiadiazolyl, 1,2,5-thiadiazolyl, 1,2,3-oxadiazolyl, 1,2,4-oxadiazolyl, 1,3,4-oxadiazolyl, 1,2,5-oxadiazolyl, 1,2,3-triazolyl, 1,2,4-triazolyl, 1H-tetrazolyl or 2H-tetrazolyl, which is unsubstituted or substituted for example by lower alkyl, such as methyl, di-lower alkylamino-lower alkyl, such as 2-dimethylaminoethyl, acylamino-lower alkyl, such as 2-acetylaminoethyl, free or esterified or amidated carboxy-lower alkyl, such as carboxymethyl, 2-carboxyethyl, carbamoylmethyl or 2-carbamoylethyl, ureidoethyl or sulfo-lower alkyl, such as sulfomethyl or 2-sulfoethyl, in particular, for example, 5-methyl-1,2,3-thiadiazol-2-ylthiomethyl, 1-methyl-1H-tetrazol-5-ylthiomethyl or 1-(2-dimethylaminoethyl)-1H-tetrazol-5-ylthiomethyl. Cephalosporins meriting special mention are: cephacetril ($R_1$=hydrogen, $R_2$=cyano, $R_3$=hydrogen, $R_4$=acetoxymethyl; The Merck Index, page 247), cefoxitin ($R_1$=hydrogen, $R_2$=thien-2-yl, $R_3$=methoxy, $R_4$=carbamoyloxymethyl; The Merck Index, page 245), cefuroxime [$R_1$=cis-methoximino, $R_2$=fur-2-yl, $R_3$=hydrogen, $R_4$=carbamoyloxymethyl, J. Antibiotics, 29, 29 (1976), Antimicrob. Agents Chemother. 9, 510 (1976)], cefazolin ($R_1$=hydrogen, $R_2$=tetrazol-1-yl, $R_3$=hydrogen, $R_4$=5-methyl-1,3,4-thiadiazol-2-ylthiomethyl; The Merck Index, page 245), cefamandole ($R_1$=hydroxy, $R_2$=phenyl, $R_3$=hydrogen, $R_4$=1-methyl-tetrazol-5-ylthiomethyl, German Offenlegungsschrift No. 2,162,575), CGP 11 481 ($R_1$=m-methylsulfonylaminophenyl, $R_2$=amino, $R_3$=hydrogen, $R_4$=methoxy, German Offenlegungsschrift 2,636,962), and the salts thereof, such as the sodium salts, and, in particular, cefotiam (=SCE-963=CGP 14 221/E, $R_1$=hydrogen, $R_2$=2-imino-4-thiazolin-4-yl, $R_3$=hydrogen, $R_4$=1-(2-dimethylaminoethyl)-1H-tetrazol-5-ylthiomethyl, for example as dihydrochloride, U.S. Pat. No. 4,080,498), and SCE-1365[$R_1$=syn-methoximino, $R_2$=2-imino-4-thiazolin-4-yl, $R_3$=hydrogen, $R_4$=1-methyl-1H-tetrazol-5-ylthiomethyl, for example as sodium salt, Chem. Pharm. Bull. 25 (11), 3115 (1977)], cefotaxime(=HR-756, $R_1$=syn-methoximino, $R_2$=2-imino-4-thiazolin-4-yl, $R_3$=hydrogen, $R_4$=acetoxymethyl, sodium salt, ibid.), and CGP 17845 ($R_1$=syn-methoximino, $R_2$=imino-4-thiazolin-4-yl, $R_3$=hydrogen, $R_4$=hydrogen, sodium salt, German Offenlegungsschrift 2,810,922). Further 7β-[2-(2-imino-4-thiazolin-4-yl)-2-methoximino- and also 2-hydroxyiminoacetamido]-cephalosporins are known from German Offenlegungsschrift Nos. 2,707,565, 2,727,753 and 2,737,504.

Suitable aminoglycoside antibiotics are also known. Their structural features are discussed in such comprehensive accounts as R. Reiner, Antibiotica, Georg Thieme Verlag, Stuttgart, 1974, pages 136–146. The aminoglycoside antibiotics are a preferred class. A group deserving of special mention is that of the kanamycins, especially kanamycin A (The Merck Index, page 692), amikacin [Mitsuhashi et al., J. Antibiotic (Japan), 27, 189 (1974), Price et al., Antimicrobial Agents+Chemotherapy, 5, 143 (1974)], dibekacin (The Merck Index, page 395) and tobramycin (ibid., page 1220), the group of the sisomicins, such as sisomicin, netilmicin (N-ethylsisomycin, German Offenlegungsschrift No. 2,437,160), SCH 22 591 (5-episisomicin, U.S. Pat. No. 4,000,261) and SCH 21420 [Antimicrobial Agents in Chemotherapy 13, 891 (1978)], and also, in particular, the group of the gentamicins, especially gentamicin C (The Merck Index, pages 565 and 566).

Depending on their solubilities and on the presence of basic and/or acid groups, the antibiotics suitable for the synergistic mixtures can be used as free compounds or as salts.

Antibiotics containing acid and basic groups can be used in the form of inner salts, i.e. in zwitter-ion form. Antibiotics of predominantly basic character can be used as stable acid addition salts, for example with inorganic acids, such as hydrochloric acid, sulfuric acid or phosphoric acid, or with suitable organic carboxylic or sulfonic acids, as with aliphatic mono-, di- or tri-carboxylic acids, for example acetic acid, malonic acid, tartaric acid, citric acid, 4-(N,N-dipropylsulfamoyl)-benzoic acid (Probenecid), with p-toluenesulfonic acid, α- or β-naphthalenesulfonic acid or naphthalene-disulfonic acid, in particular naphthalene-1,5-disulfonic acid. Antibiotics of predominantly acid character can form stable salts with bases and be used in this form. Preferred salts of this kind are in particular pharmaceutically acceptable non-toxic salts, such as alkali metal salts or alkaline earth metal salts, for example sodium, potassium, magnesium or calcium salts, and also ammonium salts with ammonia or suitable organic amines, in which latter case suitable amines for the salt formation are chiefly aliphatic, cycloaliphatic and araliphatic, primary, secondary or tertiary mono-, di- or poly-amines, as well as heterocyclic bases, for example triethylamine, hydroxy-lower alkyl amines, for example 2-hydroxyethylamine, bis-(2-hydroxyethyl)amine or tris-(2-hydroxyethyl)amine, basic aliphatic esters of carboxylic acids, for example (2-diethylaminoethyl)-4-aminobenzoate, lower alkyleneamines, for example 1-ethylpiperidine, cycloalkylamines, for example dicyclohexylamine, or benzylamines, for example N,N'-dibenzylethylene diamine, and bases of the pyridine type, for example pyridine, collidine or quinoline.

Throughout this specification, groups qualified by the term "lower", such as lower alkyl, lower alkoxy, lower alkanoyl and the like, contain not more than 7, preferably not more than 4, carbon atoms.

In a synergistic mixture of this invention, the ratio of cefsulodin sodium to the second antibiotic can vary within wide limits.

The limiting ratios of the mixture components at which synergism occurs depend on the micro-organism, the test system employed, and, naturally, on the second antibiotic. The invention provides in particular synergistic mixtures in which the weight ratio of cefsulodin sodium to the second antibiotic, with retention of the synergistic effect, is between about 1:0.001 and 1:4000.

The invention provides in particular mixtures of cefsulodin sodium (=1) with a methyleneaminopenicillin, for example mecillinam, in the weight ratio of 1:0.04 to 1:128, with a carboxy-, sulfo- or ureidopenicillin, for example mezlocillin, in the weight ratio of 1:0.04 to 1:3125, with an aminoglycoside, for example gentamicin, in the weight ratio of 1:0.004 to 1:5, in particular 1:0.06 to 1:0.09, and with a cephalosporin, for example CGP 14221/E, in the weight ratio of 1:0.0155 to 1:5.

Most particularly, the invention provides the mixtures described in the Examples.

The synergistic mixtures of the present invention are used for the manufacture of pharmaceutical preparations which contain an effective amount of the above active substance mixtures by themselves or in admixture with customary inorganic or organic, solid or liquid pharmaceutically acceptable carriers or adjuvants, for example preservatives, stabilisers, wetting agents and/or emulsifiers, solubilisers, salts for regulating the osmotic pressure and/or buffers. Such adjuvants are, for example, carbohydrates, such as saccharose, lactose, dextrose, sucrose, sorbitol, cellulose or cellulose derivatives, such as methyl cellulose, sodium carboxymethylcellulose, polyethylene glycol, polyvinyl pyrrolidone and, in particular, D-mannitol.

The pharmaceutical preparations contain 0.1 to 100%, in particular 1 to 90%, of the active substance mixture, and for convenient dosage are packed in dosage unit forms of 0.1 g to 10 g, for example in ampuls or vials. A preferred dosage form consists of dry-filled ampuls from which an injection, infusion or drip solution can be prepared, before use, by addition of the required amount of pyrogen-free water or another physiologically acceptable solvent, such as a physiological sodium chloride solution or of a plasma-containing solvent.

The pharmaceutical preparations are manufactured in the conventional manner known in the art, usually by non-chemical means, for example by conventional mixing, solution, drying or lyophilising methods.

The synergistic mixtures, or the pharmaceutical preparations which can be obtained therefrom, are administered preferably parenterally, especially intravenously, intramuscularly or subcutaneously. Administration is made either once in high doses (shock therapy), in smaller successive doses or in long-term treatment (e.g. continuous infusion). The dosage depends on the nature and degree of severity of the infection, the weight and general condition of the patient and on the mode of administration, and must be determined by the physician from case to case. In general, the dosage is between 1 and 100 mg/kg in parenteral administration.

When using synergistic mixtures containing cefsulodin sodium and an aminoglycoside, the dosage is between about 3 to 63 mg/kg, the ratio of cefsulodin sodium to aminoglycoside, for example to amikacin, being preferably about 1:0.06 to 1:0.22. When using mixtures with the more potent aminoglycosides, for example with gentamycin, the dosage is between about 3.5 to 36 mg/kg and the ratio of the components is between about 1:0.06 and 1:0.09.

The invention is illustrated by the following experimental part and the Examples, but without implying any restriction to what is described therein.

EXPERIMENTAL PART

The synergistic, i.e. more than additive, antibiotic effects were determined by means of the following experimental procedures:

1. Demonstration of the synergistic action in vitro

The combination substances A and B are diluted in DST broth OXOID in chessboard arrangement with the aid of microtitre system in 1:2 steps. All the concentrations of substance A are combined with all the concentrations of substance B and then inoculated with a standardised bacteria suspension (final concentration about $10^4$ bacilli/ml). After incubation for 18 hours at 37° C., the inhibition of the bacterial growth is determined. The inhibiting concentrations are converted by the method of Kerry et al. (J. Antimicrob. Chemotherapy 1, 417–427, 1975) into fractional inhibition concentrations (FIC), wherein an FIC of $\leq 0.7$ is taken as proof of the synergistic interaction of the combination components.

By way of example, a number of the MIC values for the action of cefsulodin sodium, mecillinam, mezlocillin and gentamicin alone against a number of micro-organisms, as well as the MIC values for a number of mixtures in which synergism occurs, are reported in Table 1.

TABLE 1

| Micro-organism | MIC (mcg/ml) | | | | |
|---|---|---|---|---|---|
| | Antibiotic A alone | Antibiotic A in combination with B | Antibiotic B alone | Antibiotic B in combination with A | FIC |
| | Cefsulodin-Na (A) | | Mecillinam (B) | | |
| Pseudomonas aeruginosa 799A | 1 | 0.25 | 1000 | 32 | 0.28 |
| Escherichia coli 12-44 | 25 | 12.5 | 2 | 0.12 | 0.56 |
| Klebsiella pneumoniae 1132 | 25 | 6.2 | 1 | 0.25 | 0.50 |
| Klebsiella pneumoniae 1136 | 50 | 12.5 | 1 | 0.25 | 0.50 |
| Proteus rettgeri 1121 | 12.5 | 0.4 | 3.2 | 1.6 | 0.53 |
| | Cefsulodin-Na (A) | | Mezlocillin (B) | | |
| Pseudomonas aeruginosa G 121 | 1.2 | 0.04 | 25 | 12.5 | 0.53 |
| Staphylococcus aureus | 3.2 | 0.2 | 3.2 | 1.6 | 0.56 |
| Klebsiella pneumoniae 1 | 50 | 25 | 1.25 | 0.16 | 0.53 |
| Proteus mirabilis 1077 | 50 | 12.5 | 1 | 0.25 | 0.50 |
| | Cefsulodin-Na (A) | | Gentamicin (B) | | |
| Proteus rettgeri 1121 | 12.5 | 0.8 | 1 | 0.5 | 0.56 |
| Pseudomonas aeruginosa 410 | 2 | 0.06 | 0.5 | 0.25 | 0.53 |
| Pseudomonas aeruginosa 1140 | 8 | 2 | 32 | 4 | 0.38 |
| Escherichia coli 576 | 64 | 32 | 2 | 0.25 | 0.63 |

2. Demonstration of the synergistic action in vivo by means of systemic infections in mice The combination substances A and B are diluted in 1:3 to 1:3.3 steps such that the average concentration contains the respective amount of substance A and substance B corresponding to the $ED_{50}$.

Female MF 2 mice weighing 18 to 22 g are divided at random into groups (n=20) and infected intraperitoneally with a standardised bacteria suspension which, according to strain, represents 5 to >20 $LD_{50}$.

Immediately after the infection, and 3 hours later, the mice are treated in groups subcutaneously with dilutions of substances A and B as well as with combinations thereof. These combinations are prepared shortly before administration by mixing each dilution of substance A with each dilution of substance B. The survival rates are determined on the fifth day after the infection. The survival rates of mice which are determined with each of substances A and B alone are compared with those obtained with the combinations of these substances. A combination which has protected more animals from death than would be expected from the independent action of the substances, is designated as having synergistic action.

The survival rates, expressed as percentages of surviving animals, found in infections with a number of pure micro-organisms and in polyinfections is reported in Table 2 for cefsulodin sodium, mecillinam, mezlocillin, gentamicin and CGP 14 221/E, as well as for corresponding mixtures.

TABLE 2

| Infective micro-organism | Antibiotic | Dose s.c. mg/kg | surviving animals (in %) |  |
|---|---|---|---|---|
| | | | Antibiotic alone | combination |
| *Escherichia coli* 205 | Cefsulodin-Na | 25 | 5 | |
| | Mecillinam | 1 | 0 | 90 |
| | Cefsulodin-Na | 20 | 5 | |
| | Mecillinam | 2 | 0 | 75 |
| | Cefsulodin-Na | 20 | 20 | |
| | Mezlocillin | 50 | 0 | 90 |
| | Cefsulodin-Na | 40 | 10 | |
| | CGP 14221/E | 0.62 | 0 | 95 |
| | Cefsulodin-Na | 20 | 0 | |
| | CGP 14221/E | 2.5 | 0 | 90 |
| *Escherichia coli* 205 $R_{TEM}{}^+$ | Cefsulodin-Na | 40 | 0 | |
| | CGP 14221/E[1] | 1.2 | 10 | 70 |
| *Klebsiella pneumoniae* 329 | Cefsulodin-Na | 40 | 0 | |
| | Mecillinam | 300 | 0 | 85 |
| | Cefsulodin-Na | 80 | 5 | |
| | Mecillinam | 300 | 0 | 100 |
| | Cefsulodin-Na | 40 | 0 | |
| | Mezlocillin | 300 | 0 | 90 |
| | Cefsulodin-Na | 50 | 0 | |
| | Gentamicin | 0.2 | 30 | 85 |
| *Klebsiella pneumoniae* 327 | Cefsulodin-Na | 100 | 0 | |
| | CGP 14221/E | 20 | 0 | 85 |
| | Cefsulodin-Na | 50 | 0 | |
| | CGP 14221/E | 40 | 0 | 85 |
| *Klebsiella pneumoniae* 329 + *Escherichia coli* 205 | Cefsulodin-Na | 100 | 0 | |
| | CGP 14221/E | 20 | 0 | 70 |

[1]7β-[2-(2-Imino-1,3-thiazolin-4-yl)acetamido]-3-[1-(3-dimethylamino)-tetrazol-5-ylthio-methyl]-3-cephem-4-carboxylic acid hydrochloride (Cefotiam)

3. Demonstration of the synergistic action in vivo by means of experimental pyelonephritis (polyinfections) in mice Mice are treated intravenously with 10 mg/kg of carrageenin. Seven days later they are infected with a standardised suspension of bacteria. One hour after the infection, 6 hours later and twice daily on each of 4 subsequent days, the mice are treated subcutaneously with the test substances alone and their combinations. Two days after the last treatment, the mice are sacrificed, dissected and examined for the number of germs in the kidneys.

The number of animals (in %) which exhibit complete clearance of the kidneys from both micro-organisms on treatment with cefsulodin sodium and gentamycin alone and in combination, is reported in Table 3.

TABLE 3

| Infecting micro-organism | Antibiotic | Lose s.c. mg/kg | Clearance of the kidneys from both micro-organisms (percentage of animals) | |
|---|---|---|---|---|
| | | | antibiotic alone | combination |
| *Pseudomonas aeruginosa* + *Escherichia coli* | Cefsulodin-Na | 25 | 0 | 70 |
| | Gentamicin | 1 | 0 | |
| *Pseudomonas aeruginosa* + *Klebsiella pneumoniae* | Cefsulodin-Na | 25 | 10 | 90 |
| | Gentamicin | 2.5 | 40 | |
| | Cefsulodin-Na | 25 | 10 | |

TABLE 3-continued

| Infecting micro-organism | Antibiotic | Lose s.c. mg/kg | Clearance of the kidneys from both micro-organisms (percentage of animals) | |
|---|---|---|---|---|
| | | | antibiotic alone | combination |
| | Gentamicin | 0.5 | 0 | 50 |

PHARMACEUTICAL PREPARATIONS

EXAMPLE 1

Dry-filled ampuls or vials containing 0.50 g of cefsulodin sodium and 0.02 g of mecillinam (1:0.04) are prepared as follows:

| Composition (for 1000 ampuls or vials): | |
|---|---|
| cefsulodin sodium | 500 g |
| mecillinam | 20 g |
| mannitol | 6 g |
| | 526 g |

The components are homogeneously mixed and an ampul or vial is filled with 0.526 g of the mixture under aseptic conditions. The ampuls or vials are sealed and tested.

Ampuls or vials containing corresponding amounts of mezlocillin, gentamicin or CGP 14221/E as second active component are prepared in the same manner.

EXAMPLE 2

Dry-filled ampuls or vials containing 1 g of cefsulodin sodium and 0.1 g of mecillinam (1:0.1) are prepared as follows:

| Composition (for 1000 ampuls or vials): | |
|---|---|
| cefsulodin sodium | 1000 g |
| mecillinam | 100 g |
| mannitol | 100 g |
| | 1200 g |

The components are homogeneously mixed and an ampul or vial is filled with 1.2 g of the mixture under aseptic conditions. The ampuls or vials are sealed and tested.

Ampuls or vials containing corresponding amounts of mezlocillin, gentamicin or CGP 14221/E as second active component are prepared in the same manner.

EXAMPLE 3

Dry-filled ampuls or vials containing 2 g of cefsulodin sodium and 0.2 g of mecillinam (1:0.1) are prepared as follows:

| Composition (for 1000 ampuls or vials): | |
|---|---|
| cefsulodin sodium | 2000 g |
| mecillinam | 200 g |
| mannitol | 200 g |
| | 2400 g |

The components are homogeneously mixed and an ampul or vial is filled with 2.4 g of the mixture under aseptic conditions. The ampuls or vials are sealed and tested.

Ampuls or vials containing corresponding amounts of mezlocillin, gentamicin or CGP 14221/E as second active component are prepared in the same manner.

EXAMPLE 4

Dry-filled ampuls or vials containing 2 g of cefsulodin sodium and 1 g of mecillinam (1:0.5) are prepared as follows:

| Composition (for 1000 ampuls or vials): | |
|---|---|
| cefsulodin sodium | 2000 g |
| mecillinam | 1000 g |
| mannitol | 300 g |
| | 3300 g |

The components are homogeneously mixed and an ampul or vial is filled with 3.3 g of the mixture under aseptic conditions. The ampuls or vials are sealed and tested.

Ampuls or vials containing corresponding amounts of mezlocillin, gentamicin CGP 14221/E as second active component are prepared in the same manner.

EXAMPLE 5

Dry-filled ampuls or vials containing 1 g of cefsulodin sodium and 1 g of mecillinam (1:1) are prepared as follows:

| Composition (for 1000 ampuls or vials): | |
|---|---|
| cefsulodin sodium | 1000 g |
| mecillinam | 1000 g |
| mannitol | 200 g |
| | 2200 g |

The components are homogeneously mixed and an ampul or vial is filled with 2.2 g of the mixture under aseptic conditions. The ampuls or vials are sealed and tested.

Ampuls or vials containing corresponding amounts of mezlocillin, gentamicin or CGP 14221/E as second active component are prepared in the same manner.

EXAMPLE 6

Dry-filled ampuls or vials containing 1 g of cefsulodin sodium and 2.5 g of mecillinam (1:2.5) are prepared as follows:

| Composition (for 1000 ampuls or vials): | |
|---|---|
| cefsulodin sodium | 1000 g |
| mecillinam | 2500 g |
| mannitol | 350 g |
| | 3850 g |

The components are homogeneously mixed and an ampul or vial is filled with 3.85 g of the mixture under aseptic conditions. The ampuls or vials are sealed and tested.

Ampuls or vials containing corresponding amounts of mezlocillin, gentamicin or CGP 14221/E as second active component are prepared in the same manner.

EXAMPLE 7

Dry-filled ampuls or vials containing 0.25 g of cefsulodin sodium and 0.937 g of mecillinam (1:3.75) are prepared as follows:

| Composition (for 1000 ampuls or vials): | |
|---|---|
| cefsulodin sodium | 250 g |
| mecillinam | 937 g |
| mannitol | 100 g |
| | 1287 g |

The components are homogeneously mixed and an ampul or vial is filled with 1.287 g of the mixture under aseptic conditions. The ampuls or vials are sealed and tested.

Ampuls or vials containing corresponding amounts of mezlocillin, gentamicin or CGP 14221/E as second active component are prepared in the same manner.

EXAMPLE 8

Dry-filled ampuls or vials containing 0.25 g of cefsulodin sodium and 1.875 g of mecillinam (1:7.5) are prepared as follows:

| Composition (for 1000 ampuls or vials): | |
|---|---|
| cefsulodin sodium | 250 g |
| mecillinam | 1875 g |

| -continued | |
|---|---|
| Composition (for 1000 ampuls or vials): | |
| mannitol | 200 g |
| | 2125 g |

The components are homogeneously mixed and an ampul or vial is filled with 2.125 g of the mixture under aseptic conditions. The ampuls or vials are sealed and tested.

Ampuls or vials containing corresponding amounts of mezlocillin, gentamicin or CGP 14221/E as second active component are prepared in the same manner.

EXAMPLE 9

In accordance with Examples 1 to 8, and using the same ratios of mixture components, dry-filled ampuls or vials can be prepared which, in addition to containing cefsulodin sodium and mannitol, contain a corresponding amount of clavulanic acid, penicillanic acid 4,4-dioxide, carbenicillin, ticarcillin, sulfocillin, azlocillin, Bay K4999, piperazillin, cephacetril, cefoxitin, cefuroxime, cefazolin, cefamandole, CGP 11481, cefotiam, SCE-1365, cefotaxime, CGP-17845, kanamycin A, amikacin, dibekacin, tobramycin, sisomycin, netilmicin, SCH-22591, SCH-21420, or a pharmaceutically acceptable salt thereof.

What is claimed is:

1. A synergistic mixture comprising cefsulodin sodium and gemtamicin C in the weight ratio of between 1:0.0008 and 1:5.

2. A pharmaceutical preparation containing an antibiotically effective amount of a synergistic mixture according to claim 1 and a pharmaceutical carrier.

3. A method of treating infections in an host comprising administering to said host an antibiotically effective amount of the pharmaceutical preparation according to claim 2.

* * * * *